(12) United States Patent
Grasser et al.

(10) Patent No.: US 8,002,464 B2
(45) Date of Patent: Aug. 23, 2011

(54) DEVICE FOR GUIDING A CABLE

(75) Inventors: Frank Grasser, Eggolsheim (DE);
Franz Schmeisser, Erlangen (DE);
Rudolf Heimberger, Würzburg (DE);
Herbert Kemeth, Hausen (DE);
Winfried Lurz, Fürth (DE); Manfred Schönborn, Gerhardshofen (DE)

(73) Assignee: Siemens Aktiengesellschaft, Munich (DE)

( * ) Notice: Subject to any disclaimer, the term of this patent is extended or adjusted under 35 U.S.C. 154(b) by 591 days.

(21) Appl. No.: 11/593,402

(22) Filed: Nov. 6, 2006

(65) Prior Publication Data
US 2007/0165786 A1    Jul. 19, 2007

(30) Foreign Application Priority Data

Nov. 7, 2005  (DE) .......................... 10 2005 053 030

(51) Int. Cl.
*H05G 1/06* (2006.01)
(52) U.S. Cl. ........................................ 378/194; 378/197
(58) Field of Classification Search ........... 378/193–198
See application file for complete search history.

(56) References Cited

U.S. PATENT DOCUMENTS

| | | | | |
|---|---|---|---|---|
| 1,586,027 A | * | 5/1926 | Campbell | 378/194 |
| 3,373,285 A | * | 3/1968 | Barrett | 378/194 |
| 4,188,540 A | * | 2/1980 | Reiniger | 378/181 |
| 5,489,010 A | * | 2/1996 | Rogers | 191/12.2 R |
| 6,065,710 A | | 5/2000 | Richter et al. | |
| 6,409,381 B1 | * | 6/2002 | Siebenhaar et al. | 378/197 |
| 2005/0152501 A1 | * | 7/2005 | Sukovic et al. | 378/197 |
| 2006/0083353 A1 | * | 4/2006 | Boomgaarden | 378/196 |

FOREIGN PATENT DOCUMENTS

| | | |
|---|---|---|
| DE | 236 832 A1 | 6/1986 |
| DE | 102 23 654 B3 | 2/2004 |
| DE | 103 32 342 A1 | 2/2004 |
| DE | 203 06 560 U1 | 7/2004 |
| DE | 20 2004 005 671 U1 | 8/2004 |
| DE | 103 08 951 B4 | 10/2005 |
| EP | 0 220 501 B1 | 5/1987 |
| JP | 01166427 A | 6/1989 |
| JP | 11168825 A | 6/1999 |
| JP | 2005054365 A | 3/2005 |

* cited by examiner

*Primary Examiner* — Hoon Song

(57) ABSTRACT

The invention relates to a device for guiding at least one cable between a first system component connected to the cable and a second system component which is relatively rotatable and/or displaceable with respect to the first and is connected to the cable, whereby the cable exhibits a cable modality which can be changed by displacement and/or rotation of the second system component, whereby at least one device for adapting the cable modality is present. By making available a guide medium which allows the device for adapting the cable modality to be guided according to the displacement and/or rotation of the second system component, it is possible to provide a device which supports a mobile device without the function of the device being restricted by the cable guide.

21 Claims, 2 Drawing Sheets

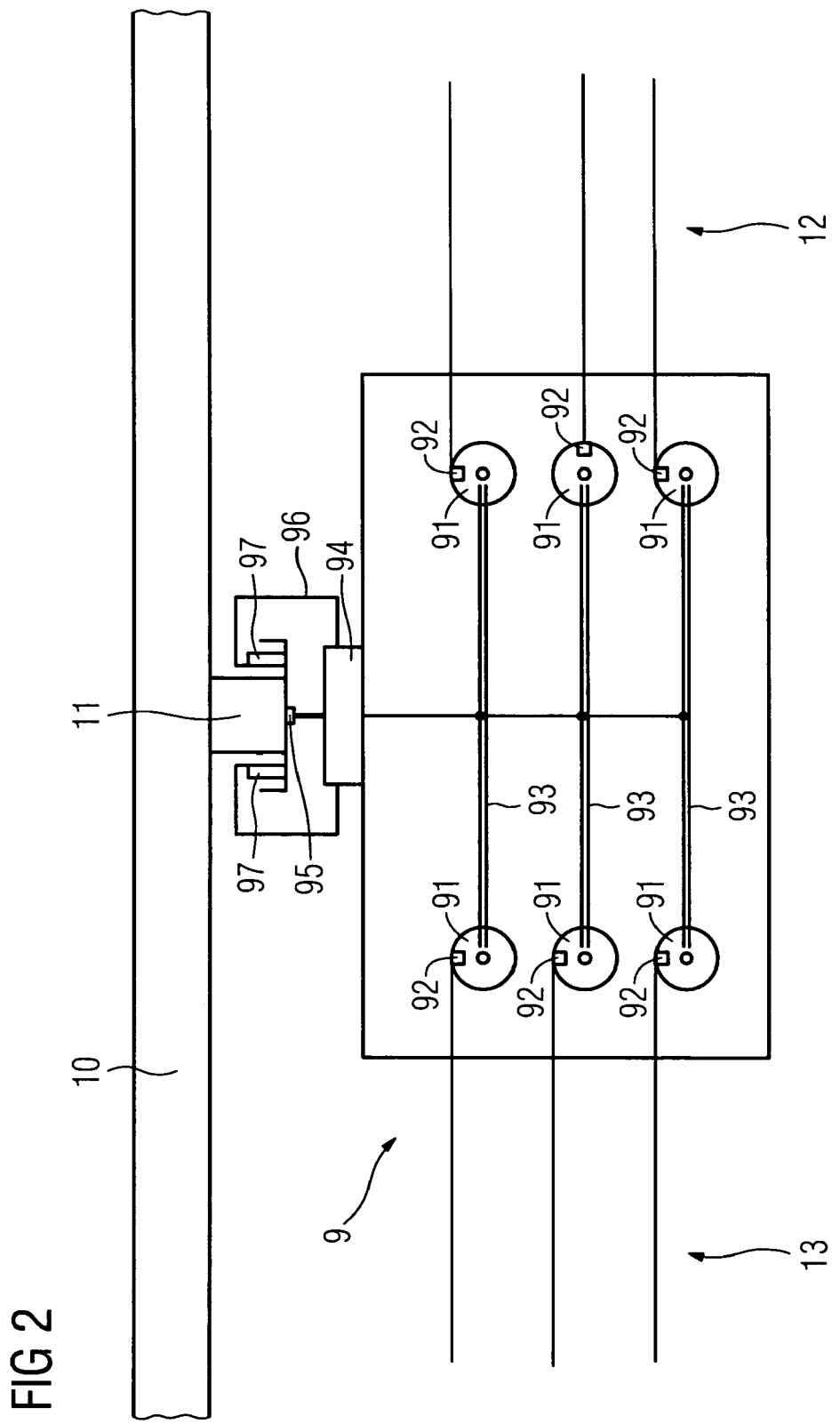

DEVICE FOR GUIDING A CABLE

CROSS REFERENCE TO RELATED APPLICATIONS

This application claims priority of German application No. 10 2005 053 030.3 filed Nov. 7, 2005, which is incorporated by reference herein in its entirety.

FIELD OF THE INVENTION

The invention relates to a device for guiding a cable between a first system component connected to the cable and a second system component which is relatively rotatable and/or displaceable with respect to the first and is connected to the cable, whereby the cable exhibits a cable modality which can be changed by displacement and/or rotation of the second system component, whereby at least one device for adapting the cable modality is present.

BACKGROUND OF THE INVENTION

When using stationary machine systems, particularly in the industrial and service technologies sectors, measures are taken in order to organize internal and external cable installations as efficiently as possible. In this situation, the aims include optimization of cable lengths and technical considerations, observance of safety requirements, etc. In this situation, the cables can for example take the form of power cables, control cables, cables for carrying gaseous and liquid fluids, in order to provide the device with the appropriate resources or the requisite data. As a result of using a device or robot with at least restricted mobility, cable guidance is made more difficult because for example the location of the device is variable or, if applicable, parts of the device connected to the cabling are pivot-mounted. The cabling must thus also be suitable for a change in position of the equipment or be designed such that no undesired interaction occurs between cabling and device and that a reliable connection is maintained. This difficulty is relevant for example to robots in manufacturing industries and also to equipment in medical engineering.

Basically, the mobility of a device has associated cost benefits since the same device can be used for the same tasks at different locations. In medical engineering in particular costs can be reduced through the use of a variable stand, in other words variable in respect of location and/or function, since it can be used for different tooling fixtures. A C-arm for X-ray diagnosis or also a patient table for example can be regarded as tooling fixtures in the field of medical engineering.

Further tooling fixtures are additionally conceivable. Other tooling fixtures can for example include mechanical arms, transport units, welding equipment, laser devices, etc. To be taken into consideration in this situation are basically all the tooling fixtures which can be used for exchangeable usage on a displaceable and/or rotatable equipment stand.

A cable guide between a fixed equipment part and a moving equipment part is known from the patent specification DD 236 832 A1, whereby a pretensioned tension spring in which the cable is guided is arranged between the two equipment parts. The length of the tension spring in the coiled state corresponds to the minimum spacing between the two equipment parts, whereby an opening for the cable is situated on the fixed equipment part, behind which opening a storage facility for spare cable is provided. One disadvantage of this cable guide lies in the tension spring present which always spans the space between the opening and the applicator, and thus on the one hand constitutes an obstacle in the space and on the other hand restricts the range of the moveable equipment within the space as a result of the mechanical load capacity of the tension spring. Furthermore, on account of the disarray of the cable in the storage facility the possibility of knotted and entwined cables cannot be excluded, which if this situation occurs can impair a movement of the applicator.

An X-ray diagnostic system with an adjustable X-ray tube, an adjustable imaging system, and a patient table as the system components and a control device for the system components is known from the patent specification EP 0 220 501 B1. In this situation, certain system components are mounted by means of sockets on the floor, ceiling and wall, on which are located levers with a power-operated rotation and swivel capability in the manner of robot arms, in order to allow universal use as far as possible. The disadvantage of this invention is the fact that the action radius of the robot arms is limited to their arm length, and these cannot be freely displaced in the space.

SUMMARY OF THE INVENTION

The object of the invention is to provide a device for guiding a cable which supports a mobile device without the function of the device being restricted by the cable guide.

The object of the invention is achieved with regard to a generic device by the fact that a guide medium is present, which allows the device for adapting the cable modality to be guided according to the displacement and/or rotation of the second system component. By this means, components of a system which are displaceable and/or rotatable relative to one another can be moved almost at will with respect to one another, whereby for example the exchange of control signals or the voltage and current supply is maintained by way of the variably adjustable cable guide.

In this situation, the cable modality, by which is understood for example the cable length and the cable torsion for a particular relative position of a first system component with respect to a second system component, is adapted by the device for adapting the cable modality. A drive device capable of being controlled by a controller can execute the displacement and/or rotation of the device for adapting the cable modality such on the guide medium that the device for adapting the cable modality assumes a position which avoids any disruption of operation of the system components resulting from an inadequately implemented cable guide.

Alternatively, the displacement and/or rotation of the device for adapting the cable modality can be effected manually on the guide medium or by means of direct control of the drive device by available personnel. This can be expedient in a situation when the system components do not change their position for an extended period of time, and thus no permanent adaptation of the position of the device for adapting the cable modality is required.

It can be advantageous for different cables, for example signal lines, gas feed lines or cables for high-voltage supply, to provide different subunits in the devices for adapting the cable modality of the cable in question, on account for example of different cable properties, such as diameter, rigidity etc. These units can be integrated in a single device for adapting the cable modality, or in different spatially separated devices for adapting the cable modality. The use of a plurality of devices for adapting the cable modality can be necessary particularly in a situation when the feed to the cable occurs from different first system components—like a gas reservoir or control unit which are separated physically from one another—or when a plurality of second system components are to be operated simultaneously in the same space.

In addition, in order to support the adaptation of the cable modality by the device for adapting the cable modality, sensors can be used which sense the position of the system components to be connected and feed this to a controller. This is particularly expedient in a situation when a permanent adaptation of the position of the device for adapting the cable modality to the position of the second system component is necessary because the second system component is constantly in motion.

In an advantageous embodiment of the invention, the guide medium is fitted to a boundary of a space. The cable guide can thus for example be implemented differently for different second system components within a space. Floor and side walls could thus be used for example for fitting the guide media for an X-ray diagnostic device in order to make possible a variable cable guide for mobile robot systems. It is also possible to adapt the guide medium concept to the mobility of the second system component.

In conjunction with a corresponding guide medium concept, fitting the cable guide to space boundaries permits a large radius of movement of the moveable second system component to be connected to the cable. In the case of space boundaries, particularly on the floor, it is always possible to integrate parts of the guide system and also parts of the device for adapting the cable modality into the space boundary in order to be able to guarantee a low space requirement and a reduced susceptibility to failure for the device according to the invention.

In particular, it is advantageous if the guide medium is fitted on a ceiling. As a result of fitting the guide medium on the ceiling, the cabling of a moveable second system component in a space at any location within the space can generally be guaranteed without causing disruption to personnel or operation of further facilities present in the space or of second system components.

Advantageously, the cable in the device for adapting the cable modality does not run generally through said device, but for example a first and a second rotatable facility for adjusting the cable length exist as parts of the device for adapting the cable modality. Thus, the length of the cable between the first system components and the first facility for adjusting the cable length and between the second system component and the second facility for adjusting the cable length can be controlled independently of one another. The respective associated cables of first and the second facilities for adjusting the cable length are connected to one another by way of a suitable connecting piece and/or a connecting space which is adapted to the requirements of the resource or information to be forwarded.

In a further advantageous embodiment of the invention, the guide medium has at least one guide rail. The number of guide rails provided and their arrangement can be matched individually to the field of application. This concerns both the spatial extent of the guide rail and also its guide concept. The guide rail can for example take the form of an air cushion rail on which the device for adapting the cable modality hovers, or for example a sliding rail in which the device for adapting the cable modality is suspended using rollers. Electrical and magnetic guide rails can likewise also be used.

If the device for adapting the cable modality is to be controlled by way of the guide rail, a conducting section of the guide rail is necessary for example, as well as a contact arrangement for the device for adapting the cable modality. Alternatively, the device for adapting the cable modality can be controlled by way of a cable-free signal connection. The guide rail can also be used for supplying power to the device for adapting the cable modality.

In a preferred variant of the invention, the guide medium has a pair of first guide rails and a second guide rail, whereby the first pair of guide rails is aligned parallel to one another and orthogonally with respect to the second guide rail. For example, the first pair of guide rails can be fitted parallel on opposite ceiling positions close to side walls, whereby the two guide rails are essentially the same length as the space. The two first guide rails are connected to one another by means of a second guide rail, whereby the second guide rail is aligned orthogonally with respect to the first guide rails. The device for adapting the cable modality is mounted such that it can be displaced and/or rotated on the second guide rail.

In a preferred embodiment of the invention, the second guide rail is mounted such that it can be displaced on the first guide rails. The entire floor area of the space is thus essentially within the travel range of the second guide rail and thus of the device for adapting the cable modality. In this situation, fitting of the guide rails is not restricted to the ceiling but can be transferred to all space boundaries.

In a further advantageous embodiment of the invention, the cable can be removed at least from one system component. As a result of having removable cabling, which can in particular be removed from at least a second system component, only a small number of devices for adapting the cable modality is required for a space. Since as a rule not all mobile second system components are operated simultaneously in a space, it is advantageous to be able to remove the cabling, bundled if possible and not individual cables, from a robot system. A next robot system can then be brought up with the device for adapting the cable modality in order to connect this to the cabling.

Advantageously, prior to or at commencement of the transportation by the device for adapting the cable modality, the cabling removed from the robot system and now hanging free can be shortened so as to exclude any danger to persons and things caused by the cable during transportation from one robot system to the next. The device for adapting the cable modality can also have a unit which performs the disconnection of the cabling from a second system component and the establishment of a new cable connection with a next second system component in an automated manner. This is expedient particularly in a situation when the second system components are assigned a fixed location in the space. Safety considerations can likewise be relevant to any automation, for example with regard to the connection of gas lines, high-voltage lines or similar. In addition, the cabling between the second system component and the device for adapting the cable modality can be given protection to protect against any external influence, for example also resulting from the individual robot system performing its function. The cabling can thus run for example in a corrugated hose or inside a metallic protective sleeve.

By preference, the device for adapting the cable modality is pivot-mounted. Thus, one the one hand, a torsion of the cabling can be reduced, which results in an increased technical reliability, while on the other hand by rotating the device for adapting the cable modality it is possible to influence the exit direction of the cabling. The latter can be used as a fine adjustment for the guidance of the cabling. In order to avoid torsion, the rotatable mounting can advantageously be located inside the device for adapting the cable modality at the cable fixing point of the reel and unreel device.

In a further advantageous embodiment of the invention, the device for adapting the cable modality has at least one reel and unreel device. By preference, inside the device for adapting the cable modality there exist at least two reel and unreel devices which separately from one another change the length of the cabling between the first system component and the device for adapting the cable modality and between the second system component and the device for adapting the cable modality. By using the reel and unreel device, it is always possible to adapt the length of the cabling to suit the requirements predetermined by the position of the system components. Further units of reel and unreel devices can be provided which are adapted to the requirements of the cabling used, such as diameter of the cable, rigidity of the cable etc.

In a further advantageous embodiment of the invention, the first system component takes the form of a controller. This is important particularly with regard to centrally controlled processes, as in the case of industrial production lines, but also in medical engineering. Thus, for example, the data from an examination carried out using a computer tomograph or a magnetic resonance device is evaluated in a central control space.

Particularly in the case of the embodiment of the second system component as a robot system or an individual robot system, which is arranged to be capable of displacement and/or rotation in an examination room, cabling to a central controller is necessary. This is because the positions of the individual robot arms must also be brought into a relationship with one another here by way of a central controller, as otherwise a patient examination with a usable result is not possible.

The main area of use of a medical robot system can for example consist in carrying out X-ray examinations but further, different tooling fixtures, such as analytical equipment, for example ultrasound equipment, laser equipment for eye treatments or accessories such as a patient table for example, can be used and operated.

In an advantageous embodiment, the robot system has a removable C-arm shaped arm for X-ray applications. Alternatively, some other desired main area of use can be chosen for the robot system. The equipment stand of the robot system is flexible in its usage, which contributes to a reduction in costs. In relation to the use of a C-arm X-ray arm and examinations with subsequent spatial representation of the examination area such as 3D angiography, instrument localizations etc., the position of the device for adapting the cable modality can be suitably adapted, by the central controller for example, to the motion of the C-arm during the examination in order to avoid any interaction or disruptive influences affecting the examination caused by the cabling.

BRIEF DESCRIPTION OF THE DRAWINGS

Further advantages of the device according to the invention are set down in an exemplary embodiment which will be described in detail in the following with reference to the drawings. In the drawings:

FIG. 2 shows a schematic illustration of a sectional view of the device for adapting the cable modality.

DETAILED DESCRIPTION OF THE INVENTION

Figure 1:
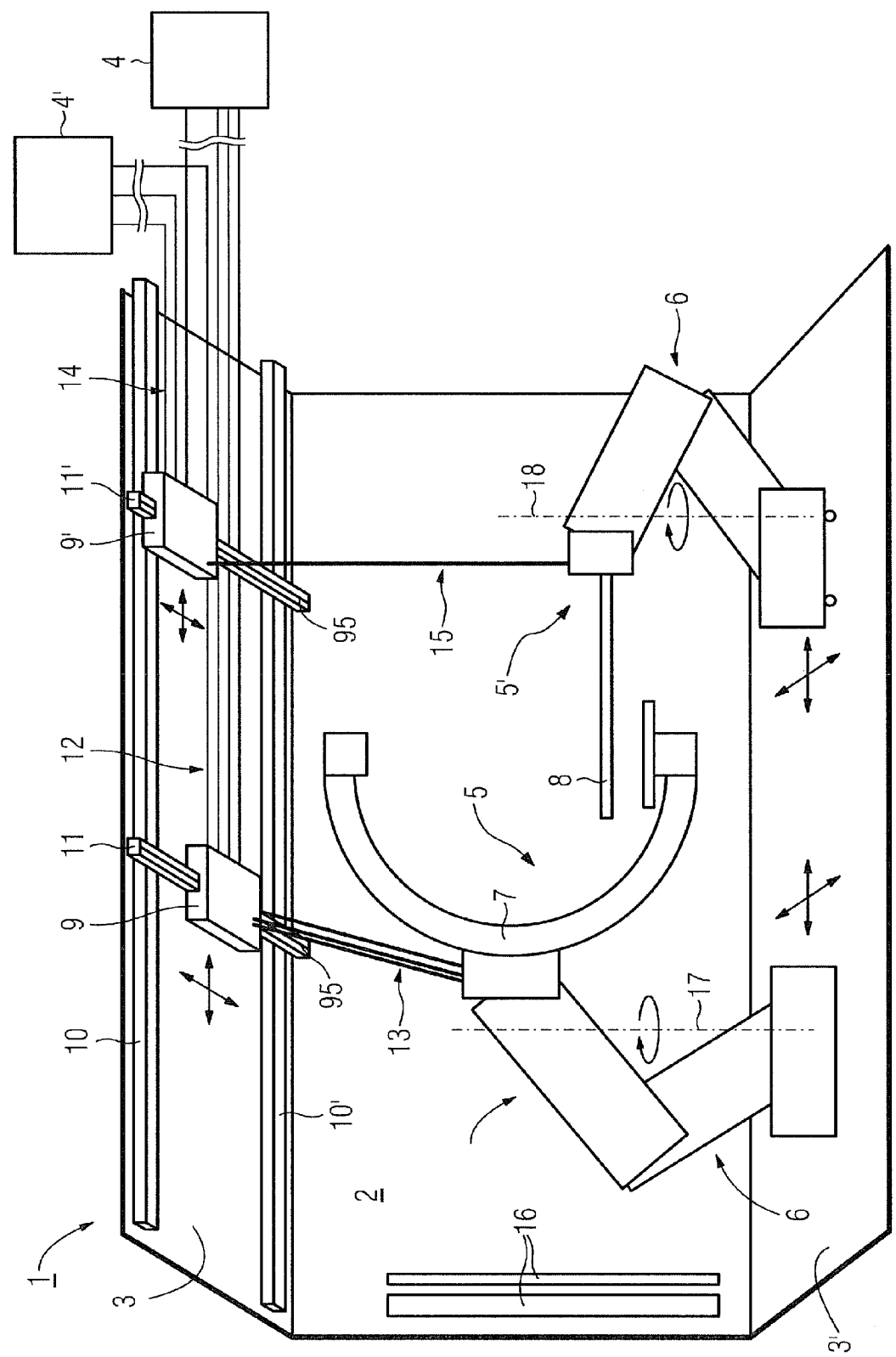
FIG. 1 shows a schematic illustration of an arrangement of the device according to the invention in a medical working environment.

FIG. 1 represents a medical working environment which comprises a space 1, whose spatial boundaries are represented partially by a side wall 2, a ceiling 3 and a floor 3'. Outside the space 1 are situated first system components 4 and 4' for a medical diagnostic system, in the form for example of a controller 4 and also a power supply unit 4'. It should be noted that, in contrast to FIG. 1, the first system components 4 and 4' may also be situated inside the same space in which a second system component 5 or 5' of the diagnostic system is situated.

The second system components 5 and 5' shown in FIG. 1 take the form of an X-ray robot system 5 and a tabletop robot system 5'. The X-ray robot system 5 consists of an equipment stand 6 and a C-arm 7 for X-ray applications. The tabletop robot system 5' similarly consists of an equipment stand 6 and a table 8. The C-arm shaped arm 7 of the X-ray robot system 5 and also the table 8 of the tabletop robot system 5' are removable and can be exchanged for further tooling fixtures 16. Further tooling fixtures 16 can take the form of means for performing medical interventions, examination devices and components thereof, storage devices for surgical instruments etc.

The X-ray robot system 5 is connected by way of cabling 13 to the first device 9 for adapting the cable modality. Furthermore, the first device 9 for adapting the cable modality is connected by way of cabling 12 to the controller 4 and the power supply 4'. The tabletop robot system 5' is connected by way of cabling 15 to the second device 9' for adapting the cable modality, which is connected by way of cabling 14 to the controller 4 and the power supply 4'.

The two devices 9 and 9' for adapting the cable modality are mounted in each case on a second guide rail 11 and 11' respectively and are mounted so as to be capable of being displaced and also pivoted along the respective second guide rail 11 or 11'. In this situation, the rotation can take place around the respective guide rail 11 or 11' and also around an axis of rotation essentially aligned perpendicular to the ceiling 3.

The second guide rails 11 and 11' are located on a pair of first guide rails 10 and 10' respectively, arranged parallel to one another, on which the second guide rails 11 and 11' can be displaced along the longitudinal extent of the guide rails 10 and 10'. The second guide rails 11 are 11' are preferably aligned orthogonally with respect to the first guide rails 10 and 10'. However, any other desired alignment of the guide rails 10 and 10' or 11 and 11' and also a further extension of guide rails are also possible. Thus, as a rule, any location within the guide plane defined by the first guide rails 10 and 10' arranged parallel to one another can be accessed by the two devices 9 and 9' for adapting the cable modality. The second guide rails 11 and 11' are advantageously arranged in such a way on the first guide rails 10 and 10' that they do not obstruct one another with regard to the travel of the respective device 9 or 9' for adapting the cable modality. All the positions for the existing robot system 5 or 5' can thus be suitably accessed by the respective device 9 or 9' for adapting the cable modality.

If the robot systems present, in other words the X-ray robot system 5 and the tabletop robot system 5' change their position or situation, then the devices 9 and 9' for adapting the cable modality are displaced accordingly and in doing so advantageously adapt the cable lengths of the cabling 12 and 14 respectively. A translatory motion and/or rotatory motion of the robot systems 5 or 5' is made possible by this means. It can be advantageous to keep constant the length of the cabling 13 or 15 between the devices 9 and 9' for adapting the cable modality and the respective robot system 5 or 5'. However, it is also possible should the occasion arise to adapt the length of the cabling 13 or 15 if this is necessary as a result of the arrangement of equipment and the accommodation. In this manner the X-ray robot system 5 or the tabletop robot system 5' can be freely moved. In particular, changes of tooling for the robot systems 5 and 5' present can be made possible as a result.

Advantageously, a cable connection platform which is not shown can be provided on the equipment stand 6, which has a standard design for all the tooling fixtures 7 or 8 or 16 that can be accommodated by the equipment stand 6. All the second system components, here therefore the robot systems 5 and 5' and with them the tooling fixtures 7 or 8 or 16, can thus be operated using standard, identical cabling, whereby there is no need to exchange the cabling for a change of tooling. The controller 4 can then control the delivery of signals or resources, according to the tooling fixtures 7 or 8 or 16 fitted on the equipment stand 6, and their resource requirements and the like.

Alternatively, the cabling 13 or 15 of the robot system 5 or 5' to the respective device 9 or 9' for adapting the cable modality can be implemented such that the equipment stand 6 and the tooling fixtures 7 or 8 or 16, for example in the manner of the table 8 or the manner of the C-arm shaped arm 7, are cabled separately. The criterion for the removability of the cable connection 13 or 15 from the tooling fixture 7 or 8 or 16 is thus necessary if the tooling fixture 7 or 8 or 16 is to be exchanged. This is then handled preferably automatically by a device which is not shown that is provided for the procedure of exchanging a cable, for example during the process of exchanging the tooling fixtures 7 or 8 or 16, or also incorporation of the new tooling fixtures 7 or 8 or 16 by the equipment stand 6. A standard cable connection platform is also expedient in this case for different tooling fixtures 7 or 8 or 16.

FIG. 2 illustrates a device 9 for adapting the cable modality, which is arranged on a second guide rail 11 to be capable of displacement and rotation. The robot-side cabling 13 and the controller-side cabling 12 are fed to the device 9 for adapting the cable modality on opposite sides of the device 9 for adapting the cable modality. In FIG. 2, both the robot-side cabling 13 and also the controller-side cabling 12 have multiple cables.

Within the device 9 for adapting the cable modality, a device 91 for adjusting the length of the cable is provided for each feed cable. In FIG. 2, the devices for adjusting the length of the cable take the form of a reel and unreel device 91. The cables are in each case connected to a reel and unreel device 91 such that, on the one hand, the cable can be reeled up and unreeled by the reel and unreel device 91 and, on the other hand, the particular cable connected can be rotated in such a manner around itself that torsion of the cable can be reduced.

The rotation of the cable is made possible by a rotatable bearing 92 forming part of the reel and unreel device 91, which reduces the shearing forces of the cable. As an alternative to a reel and unreel device 91, other means can also be used for adjusting the length of the cable which possibly utilize other principles for adjusting the length of a cable.

Alternatively, the device 9 for adapting the cable modality can be modified such that further control-side reel and unreel devices 91 are present outside the device 9 for adapting the cable modality, which set the cable length in a controlled fashion. These can for example be integrated in the ceiling 3 between the first system components and the device 9 for adapting the cable modality. The cables can thus always have their length adapted without control-side reel-up of the control-side cabling 12 inside the device 9 for adapting the cable modality. On account of the fact that the cables are not reeled up inside the device 9 for adapting the cable modality, these remain freely rotatable in a bearing device 92. The torsion of the cables can therefore similarly be reduced by such an arrangement.

In addition, FIG. 2 also illustrates the spatial separation of the robot-side reel and unreel device 91 and the control-side reel and unreel device 91. Such an arrangement of the reel and unreel devices 91 reduces the stress on the cables and makes it possible to adjust the cable length independently of the position of the device 9 for adapting the cable modality. In this situation, the forwarding of the signals, power and other resources is assured by a connecting piece 93, located within the device 9 for adapting the cable modality, between the associated reel and unreel devices 91 or the associated cables of the control-side cabling 12 and the robot-side cabling 13. The connecting piece 93 is adapted in each case to the function of the cables to be connected.

Furthermore, a drive device 94 is provided on or in the device 9 for adapting the cable modality. The drive device 94 is connected to a control line 95 which is located on the second guide rail 11. The drive device 94 on the one hand drives the device 9 for adapting the cable modality along the second guide rail 11, and on the other hand drives the reel and unreel devices 91 for the cables. If necessary, different drive devices 94 can also be provided for both functions.

In order to allow movement of the device 9 for adapting the cable modality, the device 9 for adapting the cable modality has a holding/transport device 96 which is fixed on the second guide rail 11 in a moveable fashion. The holding/transport device 96 has rollers 97 which are driven by the drive device 94 that is controlled by way of the control line 95. The device 9 for adapting the cable modality can thus be moved along the second guide rail 11. Furthermore, the drive device 94 can also drive the second guide rail 11 on the first guide rails 10 and 10' in order to move the second guide rail 11 along the first guide rails 10 and 10'. As an alternative, a separate drive device for the drive to the second guide rail 11 is also present here.

The invention claimed is:

1. A device for guiding a cable of a system in a medical procedure, comprising:
    a first system component connected to a first cable;
    a second system component connected to a second cable which is relatively movable with respect to the first system component;
    a cable adapting device sequentially connected to the first and second cables which adapts a cable modality of the first and second cables;
    a guide medium which guides the cable adapting device according to a movement of the second system component;
    wherein the cable adapting device includes at least one device which adapts a cable modality of each of the first and second cables by adjusting the length of each of the first and second cables; and
    wherein the length of each of the first and second sequentially connected cables is independently adjusted by reeling up and unreeling the cables onto or off of a reel and unreel device provided as the at least one device within the cable adapting device.

2. The device as claimed in claim 1, wherein the cable modality is a length and a torsion of each cable at a relative position of the first system component with respect to the second system component and changes with the movement of the second system component.

3. The device as claimed in claim 1, wherein the guide medium is fitted to a boundary of a space for performing the medical procedure.

4. The device as claimed in claim 3, wherein the boundary of the space is a ceiling or a side wall of a room where the medical procedure is performed.

5. The device as claimed in claim 1, wherein the guide medium comprises a guide rail.

6. The device as claimed in claim 1,
wherein the guide medium comprises two first guide rails and a second guide rail, and
wherein the two first guide rails are parallel with respect to each other and are orthogonal with respect to the second guide rail.

7. The device as claimed in claim 6, wherein the second guide rail is mounted on the first guide rail and is movable on the first guide rails.

8. The device as claimed in claim 1, wherein the first or second cable is removable from at least one of the system components.

9. The device as claimed in claim 1, wherein the cable adapting device is pivot-mounted on the second guide rail.

10. The device as claimed in claim 1, wherein the cable adapting device is adapted to a property of the cable.

11. The device as claimed in claim 1, wherein the device comprises a plurality of cable adapting devices.

12. The device as claimed in claim 1, wherein the first system component is a controller or a power supply of the system.

13. The device as claimed in claim 1, wherein the second system component is a robot system.

14. The device as claimed in claim 13, wherein the robot system is a medical examination device.

15. The device as claimed in claim 14, wherein the medical examination device is an X-ray unit comprising a removable C-arm.

16. The device as claimed in claim 1, further comprising a drive device which moves the cable adapting device along the guide medium or rotates the cable adapting device around the guide medium.

17. The device as claimed in claim 16, wherein the drive device is controlled by a controller.

18. The device as claimed in claim 1, further including rotatable bearings formed as part of the reel and unreel device, wherein the rotatable bearings allow the rotation of the cables thereby adapting a cable modality of each of the first and second cables by reducing the shear forces of the cables as they are being reeled or unreeled onto or off of the reel and unreel device.

19. The device as claimed in claim 7, wherein the device for adapting the cable modality pivots around an axis of rotation aligned perpendicular to the ceiling.

20. A method for guiding a cable of a system in a medical procedure, comprising:
connecting a first system component to a first cable;
connecting a second system component to a second cable;
relatively moving the second system component with respect to the first system component;
adapting a cable modality of the cable in a cable adapting device sequentially connected to both the first and second cables;
guiding the cable adapting device by a guide medium according to the movement of the second system component;
wherein the cable adapting device includes at least one device to adapt the cable modality of each of the first and second cables by adjusting the length of each of the first and second cables; and
wherein the length of each of the first and second sequentially connected cables is independently adjusted by reeling up and unreeling the cable onto or off of a reel and unreel device provided as the at least one device within the cable adapting device.

21. The method as claimed in claim 20, further including adapting a cable modality of each of the first and second cables by reducing the shear forces of the cables as the cables are being reeled or unreeled onto or off of the reel and unreel device by providing rotatable bearings formed as part of the reel and unreel device wherein the rotatable bearings allow the rotation of the cables.

* * * * *